(12) United States Patent
Bartko et al.

(10) Patent No.: US 9,200,987 B2
(45) Date of Patent: Dec. 1, 2015

(54) ELECTROHYDRODYNAMIC SPRAYING

(75) Inventors: Andrew P. Bartko, Columbus, OH (US); Rodney S. Black, Galloway, OH (US); James R. Busch, Columbus, OH (US); David R. Chase, Gahanna, OH (US); Ryan W. Daly, Columbus, OH (US); Theodore J. Ronningen, Lewis Center, OH (US); Matthew S. Young, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 358 days.

(21) Appl. No.: 13/580,692

(22) PCT Filed: Apr. 19, 2011

(86) PCT No.: PCT/US2011/033001
§ 371 (c)(1),
(2), (4) Date: Aug. 23, 2012

(87) PCT Pub. No.: WO2011/133516
PCT Pub. Date: Oct. 27, 2011

(65) Prior Publication Data
US 2013/0032031 A1    Feb. 7, 2013

Related U.S. Application Data

(60) Provisional application No. 61/325,641, filed on Apr. 19, 2010.

(51) Int. Cl.
*G01N 1/22* (2006.01)

(52) U.S. Cl.
CPC ............ *G01N 1/2273* (2013.01); *G01N 1/2202* (2013.01); *G01N 2001/2223* (2013.01)

(58) Field of Classification Search
CPC ................... G01N 1/22; G01N 30/724; G01N 2001/2223; G01N 1/2273; G01N 1/2202; B03C 3/011; B03C 3/38; B03C 3/40; B03C 3/45; B03C 3/53; B03C 3/68; B03C 3/76; B03C 3/36
USPC ................... 95/80; 96/52–53, 95–100, 62, 27
See application file for complete search history.

(56) References Cited

U.S. PATENT DOCUMENTS 2,949,168 A * 8/1960 Peterson .......................... 96/27
3,401,503 A * 9/1968 Bergstrom ....................... 96/39
(Continued)

FOREIGN PATENT DOCUMENTS

DE    102009020502 A1 * 11/2010 ............... B05B 7/00
WO    2005089108 A2    9/2005
(Continued)

OTHER PUBLICATIONS

International Search Report and the Written Opinion of the International Searching Authority for PCT Application No. PCT/US2011/033001: Mailing Date of Jul. 18, 2011: European Patent Office; Rijswijk, Netherlands.
(Continued)

*Primary Examiner* — Duane Smith
*Assistant Examiner* — Stephen Hobson
(74) *Attorney, Agent, or Firm* — Thomas E. Lees, LLC

(57) ABSTRACT

A small area electrostatic aerosol collector combines electrostatic collection of aerosol particles and electrohydrodynamic spraying of fluid so that a sample collected electrostatically can have fluid applied thereto. The fluid may assist with disaggregation and/or desalinization of biological material collected onto a sample substrate. A controller associated with the collector may control an electrostatic charge device and a spraying device such that the charge device and spraying device may operate in alternating fashion, or the charge device and spraying device may operate simultaneously. Further, mechanical systems are provided, for the disaggregation of particulate clusters collected onto a sample substrate.

19 Claims, 8 Drawing Sheets

(56) References Cited

U.S. PATENT DOCUMENTS

| | | | |
|---|---|---|---|
| 3,503,704 A * | 3/1970 | Marks | 423/212 |
| 4,795,330 A * | 1/1989 | Noakes et al. | 425/6 |
| 5,098,657 A * | 3/1992 | Blackford et al. | 422/73 |
| 5,173,274 A * | 12/1992 | Owen | 516/6 |
| 5,278,626 A * | 1/1994 | Poole et al. | 356/36 |
| RE34,757 E | 10/1994 | Smith et al. | 204/452 |
| 5,772,964 A * | 6/1998 | Prevost et al. | 422/70 |
| 5,813,614 A * | 9/1998 | Coffee | 239/690 |
| 5,882,591 A * | 3/1999 | Kekez | 422/28 |
| 5,914,454 A * | 6/1999 | Imbaro et al. | 95/64 |
| 5,945,678 A * | 8/1999 | Yanagisawa | 250/423 F |
| 5,994,696 A * | 11/1999 | Tai et al. | 250/288 |
| 6,005,662 A * | 12/1999 | Ence | 356/338 |
| 6,087,183 A * | 7/2000 | Zaromb | 436/178 |
| 6,105,877 A * | 8/2000 | Coffee | 239/3 |
| 6,147,345 A * | 11/2000 | Willoughby | 250/288 |
| 6,278,111 B1 | 8/2001 | Sheehan et al. | |
| 6,302,331 B1 * | 10/2001 | Dvorsky et al. | 239/3 |
| 6,391,149 B1 * | 5/2002 | Calfee et al. | 159/47.1 |
| 6,398,125 B1 * | 6/2002 | Liu et al. | 239/13 |
| 6,454,193 B1 * | 9/2002 | Busick et al. | 239/690 |
| 6,471,753 B1 | 10/2002 | Ahn et al. | |
| 6,511,850 B1 * | 1/2003 | Vigh et al. | 436/127 |
| 6,649,907 B2 * | 11/2003 | Ebeling et al. | 250/288 |
| 6,787,766 B2 * | 9/2004 | Schultz et al. | 250/288 |
| 6,797,945 B2 * | 9/2004 | Berggren et al. | 250/288 |
| 6,858,841 B2 * | 2/2005 | Truche et al. | 250/288 |
| 7,029,513 B2 * | 4/2006 | Gardner et al. | 75/330 |
| 7,150,859 B2 * | 12/2006 | Yamagata et al. | 422/508 |
| 7,391,020 B2 * | 6/2008 | Bousse et al. | 250/288 |
| 7,431,750 B2 * | 10/2008 | Liao et al. | 75/336 |
| 7,472,612 B2 * | 1/2009 | Zaromb et al. | 73/863.21 |
| 7,518,108 B2 * | 4/2009 | Frey et al. | 250/288 |
| 7,532,314 B1 * | 5/2009 | Black et al. | 356/73 |
| 7,569,812 B1 * | 8/2009 | Karpetsky et al. | 250/282 |
| 7,816,646 B1 * | 10/2010 | Willoughby et al. | 250/288 |
| 7,849,850 B2 * | 12/2010 | Atterbury et al. | 128/200.14 |
| 8,272,253 B2 * | 9/2012 | Grant et al. | 73/61.72 |
| 8,530,832 B2 * | 9/2013 | Mordehai et al. | 250/288 |
| 2001/0035494 A1 * | 11/2001 | Scalf et al. | 250/288 |
| 2002/0132362 A1 * | 9/2002 | Kaufman | 436/151 |
| 2003/0202920 A1 * | 10/2003 | Kaufman et al. | 422/186 |
| 2004/0031486 A1 * | 2/2004 | Schwarze et al. | 128/200.23 |
| 2004/0089156 A1 * | 5/2004 | Gartstein et al. | 96/53 |
| 2004/0173743 A1 * | 9/2004 | Valaskovic et al. | 250/288 |
| 2005/0126260 A1 | 6/2005 | Totoki | |
| 2006/0081728 A1 | 4/2006 | Willey et al. | |
| 2006/0110544 A1 | 5/2006 | Kim et al. | |
| 2006/0110818 A1 * | 5/2006 | Hill et al. | 435/287.1 |
| 2006/0115559 A1 * | 6/2006 | Jones, Jr. | 426/231 |
| 2006/0169887 A1 * | 8/2006 | Yamaguchi et al. | 250/288 |
| 2008/0067359 A1 * | 3/2008 | Musselman | 250/290 |
| 2008/0144003 A1 * | 6/2008 | Blackford et al. | 356/37 |
| 2009/0272892 A1 * | 11/2009 | Vertes et al. | 250/282 |
| 2010/0075317 A1 * | 3/2010 | Schneider et al. | 435/6 |
| 2010/0243885 A1 * | 9/2010 | Tepper et al. | 250/284 |
| 2010/0275780 A1 * | 11/2010 | Bailey et al. | 95/285 |
| 2011/0026018 A1 * | 2/2011 | Bartko | 356/301 |
| 2011/0159596 A1 * | 6/2011 | Keinan et al. | 436/52 |
| 2011/0315011 A1 * | 12/2011 | Black et al. | 95/79 |
| 2012/0104248 A1 * | 5/2012 | Hardman et al. | 250/288 |
| 2012/0312979 A1 * | 12/2012 | Cooks et al. | 250/282 |
| 2013/0035279 A1 * | 2/2013 | Venkataraman et al. | 514/1.1 |
| 2013/0284024 A1 * | 10/2013 | Roux et al. | 96/48 |

FOREIGN PATENT DOCUMENTS

| | | | |
|---|---|---|---|
| WO | WO 2005089108 A2 * | 9/2005 | |
| WO | 2009108795 A1 | 9/2009 | |
| WO | WO 2009108795 A1 * | 9/2009 | G01N 21/65 |
| WO | WO 2012150958 A1 * | 11/2012 | |

OTHER PUBLICATIONS van Kerckhoven; Communication under Rule 71(3) EPC for European Patent Application No. 11716778.3; dated Jun. 8, 2015; European Patent Office; Rijswijk, The Netherlands.

* cited by examiner

US 9,200,987 B2

ELECTROHYDRODYNAMIC SPRAYING

CROSS REFERENCE TO RELATED APPLICATIONS

This application is a national stage entry under 35 U.S.C. §371 of International Application No. PCT/US2011/033001, filed Apr. 19, 2011, entitled "ELECTROHYDRODYNAMIC SPRAYING", which claims the benefit of U.S. Provisional Patent Application Ser. No. 61/325,641, filed Apr. 19, 2010, entitled "ELECTROHYDRODYNAMIC SPRAYING," the disclosures of which are hereby incorporated by reference.

BACKGROUND

The present invention relates to collectors for the separation and collection of particulates from a fluid stream, and more particularly, to systems and methods that: combine electrostatic particle collection and electrohydrodynamic fluid spraying, provide electrohydrodynamic spraying inside a nozzle, provide for the application of electrohydrodynamic spraying to the disaggregation and desalination of collected samples, or combinations thereof.

The monitoring of airborne bioaerosols has received an increasing amount of attention in recent years because of the potential impact of particulates on radiative and climatic processes, on human health and because of the role particles play in atmospheric transport and deposition of pollutants. For example, it may be desirable to analyze the air in a predetermined location for particulates that fall within a range of sizes that can be inhaled, such as naturally occurring or artificially produced airborne pathogens, allergens, bacteria, viruses, fungi and biological or chemical agents that are found in or are otherwise introduced into the location.

As another example, it may be desirable to detect the presence of particular airborne particulates in semiconductor clean rooms, pharmaceutical production facilities and biotechnology laboratories to verify that there has been no contamination produced in such environments that would create undesirable environmental exposures or adversely affect manufacturing, testing or experimental processes. Similarly, the ability to detect the presence of particular airborne particulates in hospitals, nursing homes, rehabilitation centers and other care facilities may be beneficial to assist in preventing the spread of disease, infection or harmful bacteria.

The monitoring of atmospheric particulate matter further finds application for assessments of human health risk, environmental contamination and for compliance with National Air Quality Standards (NAAQS), e.g., to monitor the air in public and commercial building air purification and distribution systems; work sites such as mines, sewage facilities, agricultural and manufacturing facilities; outside areas such as street corners, flues and smokestacks; and other locations where it is desirable to monitor environmental hygiene, such as residences exposed to microorganisms, plants or animals.

BRIEF SUMMARY

According to various aspects of the present invention, a small area electrostatic aerosol collector comprises a collector housing, an aerosol entry port that provides an inlet for air to flow from outside of the collector housing to the inside of the housing, and a sample substrate receiving area within the collector housing for receiving a sample substrate upon which particulates are collected. Moreover, a passageway is provided between the aerosol entry port and the sample substrate receiving area.

Still further, the collector comprises a charging device having an electrode, a high voltage power source coupled to the charging device and a spraying device having a spray nozzle. A tip of the electrode creates an electric field defining a charging point that the air passes through between the aerosol entry port and the sample substrate. In this regard, the sample substrate is held at an electric potential that is different from the electric potential of the charging point during particulate collection. The spraying device sprays a fluid from the spray nozzle over the collection area of the sample substrate. The sprayed fluid is specifically selected to prepare the collected sample for subsequent evaluation.

In certain illustrative embodiments of the present invention, the collector comprises a pump that pulls air into the collector housing through the aerosol entry port and through the passageway such that particulates within the air drawn through the passageway are collected on a collection surface of a sample substrate, which is positioned within the sample substrate receiving area of the collector. The pump further evacuates the air stripped of particulates from the collector housing.

According to still further aspects of the present invention, a tip of the electrode of the charging device is positioned within the passageway so as to create an electric field defining a charging point that the air passes through between the aerosol entry port and the sample substrate. Additionally, the substrate is held at a neutral or opposite charge relative to the charge on the electrode. In this manner, particulates are collected on a collection surface of the sample substrate by drawing the particles to the substrate via the electric field when the aerosol is forced to flow near the substrate, e.g., via the pump. Moreover, the spray nozzle of the spraying device is positioned within the passageway between the electrode tip and the sample receiving area. A high voltage is applied to the spraying device, e.g., at least during spraying operations where the spraying device sprays a fluid from the spray nozzle over the collection area of the sample substrate.

DETAILED DESCRIPTION

Many current technologies for the monitoring and analysis of impurities require that a sample is first collected and concentrated onto a sample substrate. In this regard, according to various aspects of the present invention, a small area electrostatic collector is provided, which can be used to remove particulates including bioaerosol particles from the air and deposit them into a small area on a solid substrate. Particles are charged prior to being deposited on the substrate using electrostatic forces caused by an electric field generated within the collector. More particularly, electrostatic collection of aerosol particles is implemented by utilizing a charge source of high electrostatic potential (e.g., in the range of 8-12 kilovolts), such as a charged wire or charged needle, to charge aerosol particles that pass the charge source. The charged aerosol particles are then attracted to a substrate collection surface that is held at an electric potential different from the electric potential of the charge source during particulate collection. For instance, in some embodiments, the substrate collection surface is electrically grounded.

According to further aspects of the present invention, in numerous embodiments, the collector further comprises an electrohydrodynamic spraying device. Electrohydrodynamic spraying places a high electrostatic potential (e.g., measured in kilovolts) on conductive micro-tubing. Fluid is injected through the conductive micro-tubing such that a charge is transferred from the micro-tubing to the fluid. The transfer of charge to the fluid leads to the dispersion of the fluid in air as sub-micron diameter aerosol droplets.

According to various aspects of the present invention, devices and corresponding methods are provided for sample collection and preparation. In this regard, the electrostatic collection of aerosol particles and electrohydrodynamic (EHD) spraying of fluid are combined in a single system so that a sample collected electrostatically can have fluid applied directly thereto. In exemplary implementations, electrostatic collection of biological aerosols is accompanied by periodic or simultaneous injection of fluid, e.g., in order to prepare a collected sample for subsequent analysis. Accordingly, the collector provides integrated aerosol sampling and pretreatment of the collected sample with appropriate fluids. In other embodiments, sample preparation is further carried out by using a mechanical aid to disaggregate clusters of collected biological material.

Figure 1:
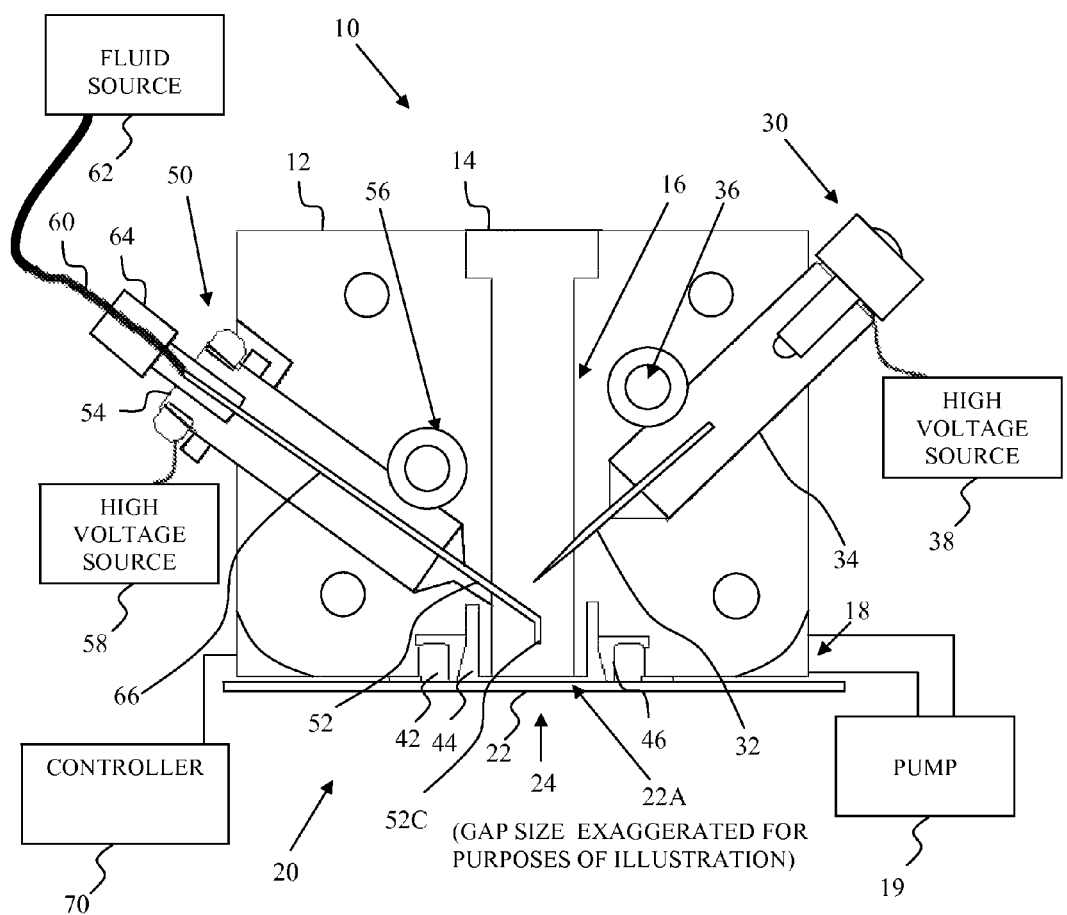
FIG. 1 is a schematic illustration of a device that combines electrostatic collection of aerosol particles and electrohydrodynamic spraying of fluid, according to various aspects of the present invention.

Referring now to the drawings and in particular to FIG. 1, a small area electrostatic aerosol collector 10 is illustrated according to various aspects of the present invention. In general, the collector 10 includes a collector housing 12 that contains electrostatic collection components, electrohydrodynamic spraying components and sample collection components as will be described in greater detail herein. The illustrated housing 12 defines a collector head base, although the housing 12 can alternatively take on other configurations. An aerosol entry port 14 serves as an inlet that provides an inlet for air to flow from outside of the collector housing 12 to the inside of the housing 12. The aerosol may be any source of gas laden with particulates to be removed from the aerosol. A typical application, however, comprises sampling ambient air.

Air to be sampled enters the aerosol entry port 14 and is moved through a passageway 16 within the housing 12. As illustrated, the passageway 16 (hereinafter, "passageway" or "ductwork") is implemented by ductwork that includes a generally tube-shaped passageway between the aerosol entry port 14 and a sample substrate receiving area. However, in other embodiments, the ductwork passageway 16 is implemented in alternate ways. As the air passes through the ductwork 16 toward the sample substrate receiving area, particulates are separated from the air, and the air (stripped of the collected particles) is exhausted from the housing 12 through an exit port. For instance, in the illustrative example, ambient air is drawn into the collector 10 through the aerosol entry port 14. The air is further drawn through the ductwork 16 and is exhausted from the collector 10 via an exhaust port 18. In several embodiments, the air is drawn through the collector 10 using a pump 19. In this regard, the exhaust port 18 should be suitably located depending upon the manner in which the sample collection process is implemented, e.g., above the sample substrate receiving area or below the sample substrate receiving area.

As illustrated, the sample substrate receiving area is implemented by a collection station 20. In general, the sample collection station 20 is utilized to collect samples of particulates extracted from the air passing through the ductwork 16 onto a collection surface 22A of a sample substrate 22 positioned within a sample collection area 24 of the housing 12.

The housing 12 is comprised of any suitable nonconductive material or materials, e.g., constructed of a polyacetal, such as Delrin® acetal resin by E. I. du Pont and Company of Wilmington, Del. Delrin is a trademark of E. I. du Pont de Nemours and Company. In many embodiments, the aerosol entry port 14 and the ductwork 16 also each comprise a nonconductive material, such as a polyacetal.

In some embodiments, the sample substrate 22 comprises an aluminized Mylar tape. The tape is oriented such that the aluminum side of the tape defines a collection surface 22A that faces the ductwork 16 so that the particulates are collected onto the aluminum. In numerous embodiments, the aluminized Mylar tape is integrated into a cassette or other format for implementation as an automated sampling system, e.g., by using a suitable roller and tensioner for winding and unwinding the Mylar tape. In other embodiments the sample substrate 22 comprises a slide such as an aluminum coated glass slide. In several embodiments, the slide is secured within the sample collection area 24 of the housing 12 using any suitable means, e.g., using a spring biased retainer that secures the slide under an air exit in the passageway of the ductwork 16 such that the slide can be easily replaced, changed, or both.

Electrostatic Collection

A charging device 30 is positioned so as to create an electric field defining a charging point that the air passes through between the inlet of the aerosol entry port 14 and the sample substrate 22. In an illustrative implementation, the charging device 30 comprises at least one electrode 32, such as a charging wire. In many embodiments, the electrode 32 comprises a tungsten electrode or other suitable material that terminates in a point or generally pointed end. As such, the electrode 32 may also be referred to herein as a charging needle to characterize the electrode as being generally "needle shaped" according to various aspects of the present invention. In general, a dull tip on the electrode may result in less efficient operation, whereas a relatively sharper tip may be more efficient. However, the specific application will dictate the requirements of the electrode geometry.

In the illustrative implementation, the electrode 32 passes through the ductwork 16 at an angle such that its tip extends generally in the middle of the passageway defined by the ductwork 16. By way of illustration, in some embodiments, the electrode 32 is positioned approximately 12 millimeters (mm) above the sample substrate 22 within a passageway of the ductwork 16. In numerous embodiments, the diameter of the passageway has dimensions of approximately 6 mm.

Moreover, the electrode 32 is supported by a collection needle holder 34. In the illustrative implementation, the collection needle holder 34 extends outside of the housing 12. This approach facilitates assembly, replacement, or both of different types of electrodes 32. Moreover, this approach facilitates positioning of the electrode 32 for desired operation, e.g., using an appropriate adjustment mechanism 36. In this regard, the adjustment mechanism 36 allows for user-adjustable control, e.g., of the angle of the electrode 32, the positioning of the electrode 32 within the ductwork 16, etc. The electrode 32 is connected to a high voltage power source 38, e.g., that generates approximately 8-12 kilovolts of direct current (dc) power, as will be described in greater detail below. In an illustrative example, the high voltage source 38 creates a high voltage signal that is connected to the collection needle holder 34 (e.g., a stainless steel housing) that couples the high voltage to the electrode 32. However, other configurations may alternatively be implemented.

According to various aspects of the present invention, the collection surface 22A of the sample substrate 22 is located in close proximity to an air exit end of the passageway 16, which is positioned opposite the aerosol entry port 14 in the illustrative example. Moreover, the collection surface of the sample substrate 22 is held at an electric potential different from the electric potential of the charge source, e.g., the electrode 32 during particulate collection. In an exemplary implementation, at least the collection surface 22A of the sample substrate 22 is held at a neutral (e.g., electrically grounded) or opposite charge relative to the electrode 32. For example, in some embodiments, a grounding ring 42, e.g., an electrically grounded copper ring, is coupled to an aluminum collection surface of the exemplary sample substrate 22. In numerous embodiments, the grounding ring 42 is grounded using a suitable ground connection and enables the sample receiving surface of the sample substrate 22 to be grounded relative to the electric field generated by the electrode 32. In this regard, in several embodiments, direct physical contact is provided between the grounding ring 42 and the collection surface 22A of the sample substrate 22 to facilitate desired grounding.

According to further aspects of the present invention, an electrohydrodynamic sleeve 44, such as an electrically grounded stainless steel sleeve, is provided around yet spaced apart from the end section of the ductwork 16, and a head seal 46, such as a rubber gasket, is positioned between the grounding ring 42 and the electrohydrodynamic sleeve 44. In an exemplary implementation, the head seal 46 comprises a gasket that isolates the region of the sample substrate 22 oriented with respect to the end of the ductwork 16 for receiving particulates so that the collection area is isolated during sample collection, e.g., so that previously collected samples are not contaminated by particulates collected during a current collection process. Thus, multiple collection sites are possible on a single sample substrate.

In operation, the pump 19 pulls air into the collector housing 12 through the aerosol entry port 14. The air is drawn by the pump 19 from the inlet of the aerosol entry port 14 through ductwork 16. A tip of the electrode 32 associated with the charging device 30 is positioned within ductwork 16 so as to create an electric field defining a charging point that the air passes through between the aerosol entry port 14 and a sample substrate 22. Further, the collection surface 22A of a sample substrate 22 positioned within the collector station 20 is held at an electric potential that is different from, e.g., held at a neutral or opposite charge relative to, the electric potential of the charging point defined by the charging device 30 during particulate collection. The charged particles are attracted to, and are thus likely to adhere to, the collection surface 22A, thus providing improved collection efficiency. Particulates are thus collected by containing the aerosol in a small area within the ductwork 16 and by forcing the aerosol to flow near the sample substrate 22 such that the charged particulates are attracted to the collection surface 22A of the sample substrate 22.

In many embodiments, the pump 19 further evacuates the particulate-free air through the exit port 18. The pump 19 evacuates the air out of the sample collection station 20 and, optionally, out of the housing 12 to atmosphere. In this regard, the sample substrate 22 is positioned in close proximity to the exit end of the ductwork 16 and the main pressure change occurs at the gap between the ductwork 16 and the sample substrate 22, which may be barely big enough for the air to pass through. In an illustrative example, the pump pulls between approximately 1-3 liters of air per minute.

Particulates in the air are charged when they pass the electrode 32 and are attracted to the oppositely charged (or grounded) collection surface 22A of the sample substrate 22. The remaining air is evacuated, as noted in greater detail herein. In this regard, air is not required to flow under/behind the sample substrate 22. Rather, air may flow under/behind the sample substrate 22 for exhausting from the collector 10 housing 12. Alternatively, air may be directed from above the collection surface 22A of the sample substrate 22, so as to be drawn through an air passageway, e.g., the passageway 18, to a location outside of the collector housing 12. Evacuation of air from above the sample collection surface 22A may be of interest, for example, where the sample substrate is implemented using automated processes, such as collection tape based systems.

When high dc voltage, e.g., a dc voltage in the range of 1,600 volts to over 11,000 volts, is applied to the electrode 32, a corona discharge extends from the point of the electrode 32 (point emission electrode) to the substrate 22. The collection surface 22A of the sample substrate 22 is grounded or held at a charge opposite of the electric field generated within the ductwork 16. As such, the sample substrate 22 forms a discharge electrode. An electric field charges particulates suspended within the air stream passing through the ductwork 16 towards the sample substrate 22. Moreover, precipitation takes place between the electrode 32 and the sample substrate 22, and the particulates within the aerosol are collected onto the sample receiving surface of the sample substrate 22.

According to various aspects of the present invention, no heat or other feature is required to prevent precipitation in the ductwork 16 itself. Moreover, the material of the ductwork 16, e.g., Delrin® acetal resin in the above example, is useful in reducing, preventing or otherwise inhibiting any potential precipitation/buildup in the passageway. Moreover, the collector 10, according to various aspects of the present invention, does not necessarily run in a continuous manner. Rather, there may be stops in the collection process, which allows time for the electrode 32 to dissipate. Since the field generated by the electrode 32 has time to dissipate, the potential for contamination build up within the collector is minimized.

Electrohydrodynamic Spraying

The collector 10 also includes an electrohydrodynamic spraying device 50. The illustrated electrohydrodynamic spraying device 50 comprises an electrohydrodynamic spray nozzle 52, e.g., a conductive micro tubing, for spraying fluid towards the sample area. For instance, as illustrated, the spray nozzle 52 extends into the passageway between the tip of the electrode 32 and the sample collection surface.

The spraying device 50 further comprises an electrohydrodynamic nozzle holder 54 that passes through the body of the housing 12. The nozzle holder 54 is charged to a high voltage in a manner analogous to that described in reference to the Electrostatic Collection above. In an exemplary implementation, an adjustment device 56 is provided to adjust the position of the nozzle holder 54 and hence, the spray nozzle 52 within the ductwork 16 to facilitate proper setup, also in a manner analogous to that described in reference to the Electrostatic Collection above. In alternative implementations, the adjustment device 56 is either optional or not implemented. For instance, depending upon the implementation, the adjustment device 56 can be utilized for one or more of the following: to adjust the angle of the spray nozzle 52 within the ductwork 16, to adjust the amount of penetration of the nozzle into the ductwork 16 or to facilitate user replacement of the spray nozzle 52.

A high voltage source 58 is provided to couple a high voltage to the spraying device 50 and corresponding spray nozzle 52. In an illustrative example, the first and second power supplies 38, 58 comprise different power supplies. For instance, two power supplies are be utilized in tandem. Under this configuration, the first and second power supplies generate voltages relative to a different reference potential. Alternatively, the first and second power supplies 38, 58 can each generate a high voltage with respect to a common ground reference. As yet another alternative example, the first and second power supplies 38, 58 are implemented by a single power source that is optionally scaled to provide the appropriate voltage to the electrode 32 and the spray nozzle 52. Still further, as will be described in greater detail below, in certain illustrative embodiments, the voltage of each of the first and second power supplies 38, 58 is controllable, e.g., switchable between two or more voltages. For instance, a controller may control each voltage source 38, 58 for operation between an off state, a high voltage state and an operating state, where the output at the high voltage state is a relatively high voltage that is different from (e.g., less than) the operational voltage setting.

A fluid tubing 60 feeds fluid from a suitable source 62 such as a syringe pump, into the spraying device 50, e.g., using a suitable fluidics fitting 64. The end of the spraying device 50 proximate to the fluidics fitting 64 thus defines a fluid inlet to the spraying device 50. The fluid is injected from the fluidics fitting 64 through a spray-fluid passageway 66 in the nozzle holder 54, e.g., a conductive micro-tubing such as stainless steel. Electrohydrodynamic spraying places a high electrostatic potential (e.g., measured in kilovolts) on the spray-fluid passageway 66. In response thereto, a charge is transferred from the spray-fluid passageway 66 to the fluid. The spray nozzle 52 sprays the charged fluid towards the sample collection area 24. The charge in the fluid disperses the fluid in air as aerosol droplets with sub-micron diameters.

According to various aspects of the present invention, particulates are collected on a collection surface 22A of the sample substrate 22 by containing the aerosol in a small area within the ductwork 16 and by forcing the aerosol to flow near the substrate via the pump 19. Additionally, the spraying device 50 sprays a fluid over the collection area 22A of the sample substrate 22, where the fluid is specifically selected to prepare the collected sample for subsequent spectroscopic evaluation.

There are several benefits to combining electrostatic collection and electrohydrodynamic spraying into a single collection system. For instance, the collected sample does not have to be moved to a sample preparation station in order to suitably prepare a sample of analysis. Such an arrangement saves not only time, but also the space within a system that would otherwise be required for separate sample collection and preparation stations.

According to still further aspects of the present invention, the collector 10 includes a controller 70, which is coupled to the charging device 30, the spraying device 50, or both. The controller 70 can thus control the charge device 30 and the spraying device 50 in any number of suitable manners. In certain embodiments, the controller 70 also controls aspects of sample substrate preparation, e.g., by advancing or otherwise controlling a mechanism to wind a sample collection tape into suitable position for sample collection. By way of a first illustration, the controller 70 controls the collector 10 such that collection and spraying takes place in an alternating fashion, i.e., collect for a period, spray for a period, collect again, spray again, etc. As yet another alternative example, the controller 70 controls the collector 10 such that sample collection and spraying occurs effectively or substantially simultaneously, e.g., wherein particles may intermingle with the fluid droplets in the air before accumulation on the collection surface 22A of the sample substrate 22.

In practice, specific geometric configurations and operating conditions may provide more optimal response characteristics, e.g., to allow for electrostatic collection and electrohydrodynamic spraying to be used in the same nozzle. For instance, as illustrated, the fluid injection nozzle 52, e.g., a metal micro-tubing, e.g., having an outside diameter of approximately 500 microns, is placed below the electrostatic charging electrode 32. More particularly, the exit end of the spray nozzle 52 is closer to the collection area 22A of the sample substrate 22 than the tip of the electrode 32. In a further illustrative exemplary implementation, the electrode 32 and the exit end of the spray nozzle 52 is spaced apart by a predetermined distance to prevent conduction there between. In an illustrative example, a separation of at least 6 millimeters may be sufficient to avoid conduction between the two. One exemplary approach to conserve space is to place a bend in the spray nozzle 52 such that the exit end of the spray nozzle 52 is sufficiently separated from the electrode 32.

For example, as illustrated, the spray nozzle 52 of the spraying device 50 includes a bend along its length positioned within the ductwork 16 such that the spray nozzle 52 enters the ductwork 16 at an angle, e.g., non-perpendicular to the wall of the ductwork 16, and an exit of the spray nozzle 52 points substantially down towards the collection area of the sample substrate 22. In an illustrative example, the spray nozzle 52 contains a bend of an obtuse angle, e.g., a bend at an obtuse angle in a metal micro-tubing for dispensing a fluid towards the sample area. In this regard, the spray nozzle 52 comprises an end portion 52C for injecting fluid that points towards the grounded collection surface 22A of the sample substrate 22. In the illustrative example, the end portion 52C is arranged substantially parallel to the walls of the ductwork 16 proximate to the sample substrate 22. Moreover, in certain illustrative embodiments, the end portion 52C extends a distance, e.g., approximately 1 millimeter, and can optionally include a bend so that the opening of the spray nozzle 52 points towards the deposition surface of the sample substrate 22.

In yet another illustrative example, electrostatic collection occurs when the tip of the electrode 32 is approximately 12 mm above the collection area 22A of the sample substrate 22. There may be at least 6 mm separation between the tip of the electrode 32 and the exit 52C of the spray nozzle 52. Thus, the exit 52C of the spray nozzle 52 is positioned within 6 mm of the collection surface 22A of the sample substrate 22.

As yet a further illustrative example, the electrode 32 and the spray nozzle 52 enter the ductwork 16 from different, e.g., substantially opposite sides of the ductwork 16, such that only the tip of the electrode 32 and the exit end of the spray nozzle 52 extend at least substantially to a position above the center of the collection area of the sample substrate 22. For instance, the electrode 32, e.g., a charging needle, and the spray nozzle 52, enter the ductwork 16 from opposite sides such that only the tip of the charging electrode 32 and the exit end of the spray nozzle 52 overlap in the ductwork 16 above the center of a collection region associated with the collection surface 22A of a sample substrate 22 loaded into the collection station 20.

For both electrostatic collection and electrohydrodynamic spraying, the highest charge density is centered above the target zone defined by the collection surface 22A. This presents the problem of charge transfer between the charged elements, i.e., the electrode 32 and the spray nozzle 52. However, placing the fluid injection nozzle below the electrostatic charge needle, maintaining suitable separation between the charged elements to prevent conduction there between, suitably reducing the potential difference between the charged elements, or combinations thereof, suitably addresses these charge transfer problems.

As noted in greater detail herein, separation of the conductive elements can optionally be achieved by placing a bend in the fluid injection nozzle such that the tip of the fluid injection nozzle is sufficiently separated from the tip of the charging needle. Additionally, by inserting the charging needle and the fluid injection nozzle from opposite sides, only the tips of the charging needle and fluid injection nozzle overlap, e.g., in the center of the collection region. Moreover, according to certain embodiments of the present invention, the controller 70 holds the charge device 30 at a high voltage when the spraying device 50 is being operated and the controller 70 holds the spraying device 50 at a high voltage when the charge device 30 is being operated where the voltages are selected to avoid conduction between the charge device 30 and the spraying device 50. Thus, even when only one of the two elements, e.g., the charge device 30 and spraying device 50, is operating, the other element may still be held at a high electrostatic potential (although not necessarily at its operating potential) in order to prevent conduction between the two.

Spray Nozzle

For electrohydrodynamic spraying, fluid is pumped through the spray nozzle 52. Voltage, e.g., from the voltage source 58, is applied to the spray nozzle 52, e.g., a metal micro-tube, which causes fluid that has entered the spraying device 50 via the fluid tubing 60 to form a Taylor cone as it emerges and disperse as aerosol droplets.

In conventional electrohydrodynamic spraying applications, consistent electrohydrodynamic spraying can be achieved, e.g., in a "free space" configuration, e.g., with no surfaces within several centimeters of the charged tubing of the spray nozzle 52 or the dispersed aerosol. However, the space within the collector 10 about the spray nozzle 52 is a "closed space." As such, conventional electrohydrodynamic spray techniques may result in the injected fluid flowing as a stream towards this surface instead of forming the Taylor cone and dispersing.

According to various aspects of the present invention, the spray nozzle 52 is utilized for electrohydrodynamic spraying of a fluid inside an enclosed area of the ductwork 16. In this regard, in an illustrative example, the diameter of the ductwork is on the order of 6 mm, however other dimensions may alternatively be implemented.

However, according to various aspects of the present invention, consistent electrohydrodynamic spraying is achieved despite being positioned inside an enclosed cylinder that has an inner diameter of only several millimeters. To achieve consistent electrohydrodynamic spraying, as noted above, the spray nozzle 52 is implemented in some embodiments using metal micro-tubing. Moreover, the exit 52C of the spray nozzle 52 is bent so as to point towards the grounded deposition surface, i.e., the exit 52C of the spray nozzle 52 is parallel to the walls of the cylinder shaped ductwork 16 and is perpendicular to the sample substrate 22. As also noted in greater detail herein, in illustrative embodiments, the spray nozzle 52 enters the cylinder through a side wall; however, the tip (e.g., approximately 1 mm from the exit end) is bent so that it points towards the deposition surface for flowing the liquid.

Figure 2:
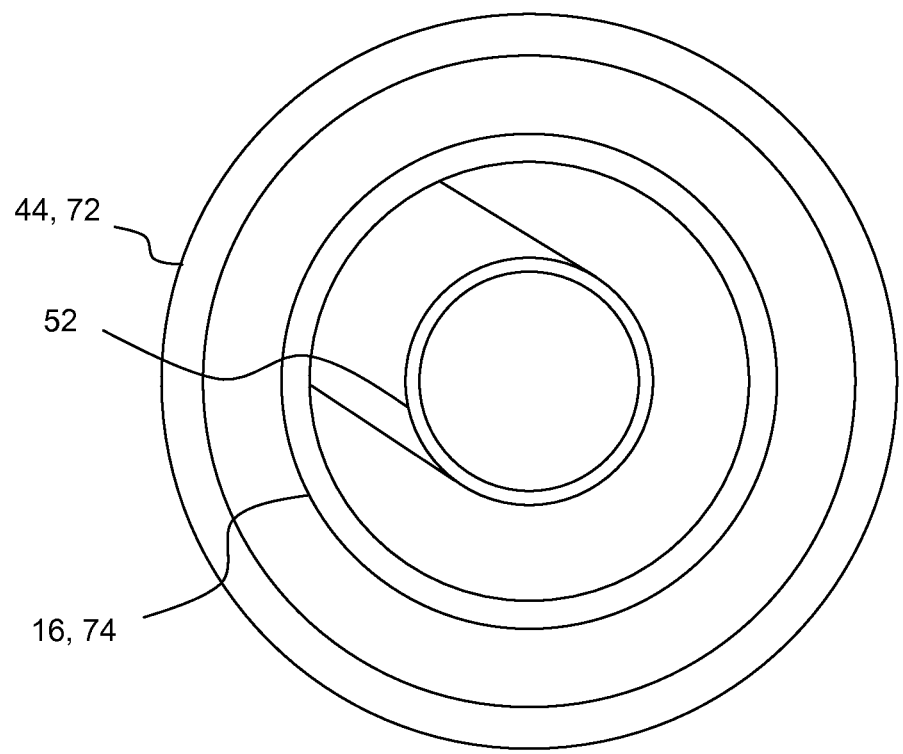
FIG. 2 is a view looking up from the bottom toward an exit end of a spray discharge nozzle of a spraying device according to various aspects of the present invention.

Referring to FIG. 2, a view is presented looking up from the bottom of the collector 10, according to further aspects of the present invention. As schematically represented, in this illustrative but non-limiting implementation, the spray nozzle 52 is positioned inside two cylinders, which are concentric. More specifically, the spray nozzle 52 is positioned within an outer cylinder 72 and inner cylinder 74. The inner concentric cylinder 74 is closest to the charged injection tubing, is generally cylindrical in shape and is constructed so as to be a non-conductive cylinder, e.g., a Delrin or similar material. In this regard, the inner concentric cylinder (Delrin collector head) comprises the ductwork 16 and may thus have a diameter in an exemplary implementation, on the order of approximately 6 mm. The nonconductive cylinder 74, which is closest to the charged injection fluid tubing 60 and corresponding spray nozzle 52, defines a collector head and is non-conductive in order to insulate the charged fluid tubing 60 and spray nozzle 52.

The outer cylinder 72 comprises an external conductive cylinder. For instance, referring back to FIG. 1, the outer cylinder 72 may be implemented as the electrohydrodynamic sleeve 44, which is spaced from and optionally concentric with the ductwork 16 proximate to the sample collection area. In the illustrative example, the electrohydrodynamic sleeve 44 is electrically grounded and extends sufficiently within the housing 12 to surround the exit end of the spray nozzle 52. Under this illustrative configuration, the spraying device 50 produces a consistent aerosol dispersion and electrohydrodynamic spraying produces a dispersion of sub-micron diameter aerosol droplets, even at low fluid flow rates, e.g., on the order of micro liters per minute.

As described more fully herein, the use of a bent metal micro-tubing for flowing the liquid sample, the use of two concentric cylinders, an internal non-conductive cylinder and an external conductive cylinder, and combinations thereof, provide the device with the ability to achieve consistent aerosol spraying, as described more fully herein.

Sample Preparation

According to various aspects of the present invention, electrohydrodynamic spraying of fluids may be applied to the preparation of dry, collected biological aerosol samples. In this regard, the spraying of fluids can disaggregate clusters of the collected biological material and/or desalinization of the collected biological materials.

Biological aerosols collected from the atmosphere have at least two characteristics that make them difficult to analyze using spectroscopic techniques such as Raman spectroscopy. The aerosol particles are often agglomerations of biological materials, e.g., several bacterial cells agglomerated into a cluster. In Raman analysis, it is beneficial to probe individual cells or, at least, small clusters (0.5-1.5 micrometer diameters). Moreover, the biological aerosol particles also often have inorganic salts intermingled with the biological material of interest. Crystallized, polyatomic salts often have strong Raman responses that make the Raman spectrum of the biological material more difficult to analyze. Therefore, it is beneficial to either separate the salts from the biological material or dissolve the salts prior to Raman analysis since the dissolved salts do not have a strong Raman response.

However, according to various aspects of the present invention, electrohydrodynamic spraying is utilized in the electrostatic aerosol collector 12 as an effective means of accomplishing disaggregation of clusters of the collected biological material, desalinization of the collected biological materials, or both. Thus, electrohydrodynamic spraying according to various aspects of the present invention, provides a means of generating a dispersion of sub-micron diameter aerosol droplets at low fluid flow rates, e.g., on the order of microliters per minute. This mist is generated by injecting the fluid across a large electrostatic potential (measured in kilovolts), with the injection micro-tubing at a raised potential and the target surface at electrical ground. The generated dispersion spreads out over a sufficiently large area that all of the collected aerosol particles can be covered with fluid in a single spray.

In an illustrative example, the fluid comprises a mixture of water with ethanol, such as a mixture comprising water with 20-35% ethanol. However, other fluid mixtures may also be applicable. Electrohydrodynamic spraying could inject other fluids so long as enough water is available that the salts will dissolve in the fluid but also a sufficient percentage of organic solvent is available in order to prevent the water soluble biological material from dissolving as well.

Electrohydrodynamic spraying onto biological clusters encourages these clusters to separate, leading to significant separation of agglomerated particles, even within tens of seconds to minutes of spraying. The deposited fluid is also able to evaporate quickly, without pooling into large droplets that might lead to significant movement of the biological material on the substrate.

Applications of various aspects of the present invention find use for example, in the treatment of collected biological aerosol samples in preparation for spectroscopic analysis, e.g., Raman analysis. Other analysis techniques that benefit from analyzing separated biological particles and/or biological particles free of salt would also benefit from applying various aspects of the invention as set out in greater detail herein.

Illustrative Examples

As an illustrative example, a 1 milliliter (ml) plastic syringe, e.g., by Becton, Dickinson and Company of Franklin Lakes, N.J. was tested with an 18-gauge flat tip needle utilized to implement the spray nozzle 52, e.g., by Engineered Fluid Dispensing (a Nordson Corporation of Westlake, Ohio) at a vertical distance of approximately 1 inch (2.54 centimeters) from the sample substrate 22. A solution of 50% EtOH, e.g., 20 ml ethanol and 20 ml $H_2O$, was sprayed at an infuse rate at 0.5 microliters per second (µl/sec) (30 µl/min). In this illustrative implementation, a Taylor cone and fine mist spraying was achieved at 5-6 kilovolts (kV). If the voltage is too low or too excessive, the spray pattern quality can deteriorate, e.g., into a spitty spray, split into a multi section beam, etc. Lowering the infusion rate, e.g., to 0.25 µl/sec (15 µl/min) at 5-6 kV resulted in even a finer spray. Under this configuration, the outside diameter of the spray was about 15 mm.

Reducing the distance of the needle spray nozzle 52, e.g., down to approximately half an inch (12.7 mm) above the sample substrate 22 resulted in a well-sprayed pattern at 4-5 kV. Moreover, spraying was successful at both 0.25 µl/sec and 0.5 µl/sec. In another illustrative example, a 5.0 µl dose appeared to wet the sample area well, e.g., enclosed in a 6 mm diameter.

A small, e.g., about 5 mm, length of flexible tubing or other suitable material is optionally placed over the flat tip of the needle. Moreover, the needle is optionally turned horizontally, e.g., using an appropriate adjustment mechanism 56. However, when using the needle turned horizontally, a bend about its tip (e.g., 52C of the spray nozzle 52) of substantially 90 degrees is preferable. However, the bent tip may skew the spray pattern away from the high voltage field, even at lower voltages.

In general, spray divergence may be dependent upon a number of factors, including for example, the needle diameter. Moreover, the flow rate will determine wetting. For instance, a flow rate of 1 µl/min may spray fine but result in a wetting that is barely visible, e.g., compared to a flow rate of approximately 5 µl/minute, which may result in a wetting that is visible on the surface of the sample substrate. Moreover, the flow rate may affect that shape of the spray pattern. For instance, relatively low flow rates may result in a wetting that is more elliptical in shape, whereas increasing the flow rate may eventually restore the shape of the sprayed area to a substantially circular pattern.

Still further, in certain embodiments, the needle sprays in air. However, a collar is optionally utilized, e.g., an insulation material can be placed over the sample substrate, such as to define a boundary for the spray pattern. In some embodiments, the ductwork 16 serves a further purpose of defining a boundary for the spray pattern. In other embodiments, a tube of conductive material forms a spray boundary and a grounding feature 44, which does not necessarily touch the sample substrate 22 and is described in greater detail herein.

Still further, by angling the needle implementing the spray nozzle 52 into the ductwork 16, the pattern of spray on the sample substrate may be made oblong, elliptical, etc. Still further, the needle end may affect spraying. For example, a hypodermic needle with a beveled exit aperture may affect the spray pattern. As such, the spray pattern of the spraying device may be controlled by at least one of the flow rate of the corresponding fluid, the angle of the needle implementing the spray nozzle 52 and the geometry of the spray nozzle end.

Figure 3:
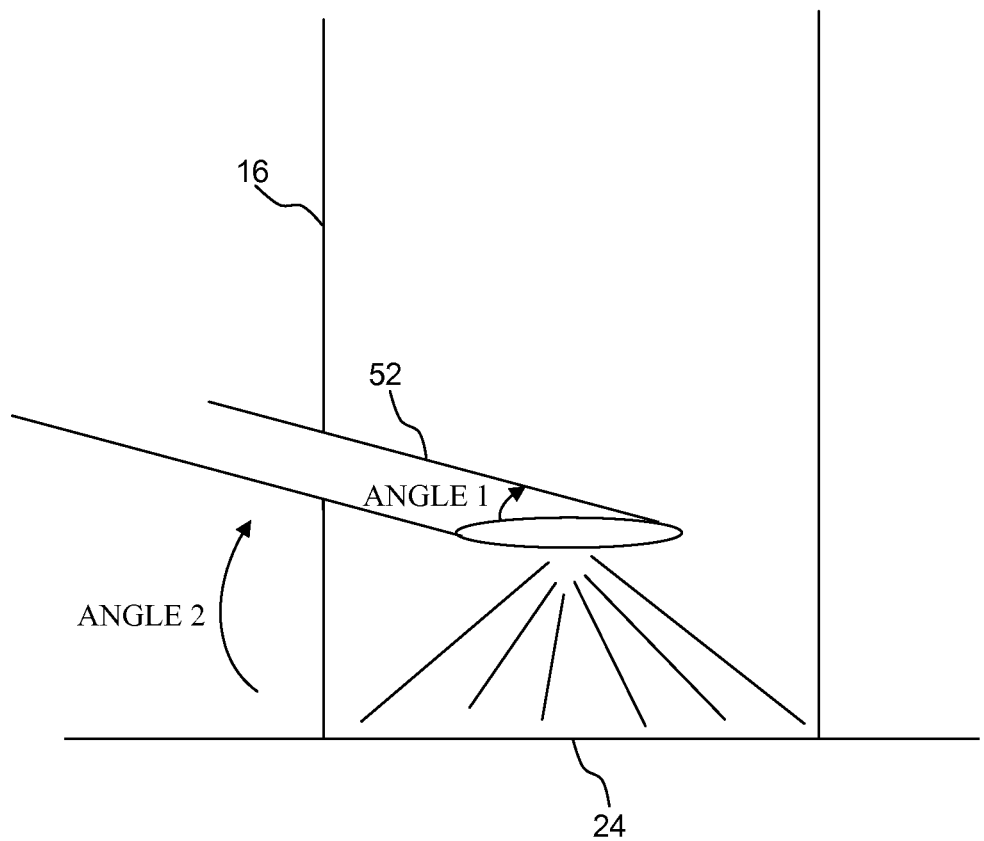
FIG. 3 is a schematic illustration of a beveled needle spraying a sample substrate within a collector according to various aspects of the present invention.

Referring to FIG. 3, when using a hypodermic needle as the spray nozzle 52, the needle has a beveled needle exit at a first angle ANGLE 1 that should be accounted for when adjusting the needle to a corresponding installation angle ANGLE 2. For instance, a beveled needle achieves an oblong spray pattern having a long axis perpendicular to the needle axis.

In an illustrative implementation, using a 20 mil (500 µm) outside diameter spray nozzle 52 at an air flow rate of 3.0 l/min and a 25% EtOH fluid flow rate of 5.0 µl/min., a steady spray may be achieved from 4.0-6.0 kV, with a largest spot of less than 5 mm at 4.5-5.0 kV. Under this approach, a 5 mm spot may take less than 1 minute to dry. Adjusting the spray nozzle 52 to about 1.5 mm from the edge, a nice spray may be achieved from 5.0-5.5 kV, almost covering the whole 6 mm spot.

Mechanical Aid to Disaggregate Clusters of Collected Biological Material

For the analysis of biological materials it is sometimes necessary to break up clusters of aggregated cells, or other biological material, into individual cells. According to various aspects of the present invention, such can be accomplished using electrohydrodynamic spraying (as described above), mechanical means, or both. As an illustrative example, a motor can be used to shake and separate such clusters by shaking the substrate they are collected on.

Biological material, such as bacterial cells, often aggregate into clusters when it is dried. For some types of analyses, such as counting the number of cells or microscopic analysis of individual cells, it is valuable for such clusters to be broken up and for individual cells to be separated. This can be done by shaking the substrate that contains the clusters, which transfers the kinetic energy into the clusters. The vibrations resulting from the kinetic energy separate the aggregated cells from one another.

According to various aspects of the present invention, systems and methods are provided for shaking the sample substrate and the clusters using a motor, such as a cell phone vibration motor, as a compact and relatively low power driver. Exemplary motors comprise, for example, Precision Microdrives #310-101 (a 10 mm diameter button-type at 12 kHz) and #304-002 (a 4 mm×8 mm off-center shift weight design).

In this regard, such a feature allows the cluster separation to be integrated efficiently into an instrument, thus saving the time required to later perform the disaggregation process and also to save the space typically required to perform such a step at a separate station.

Figure 4:
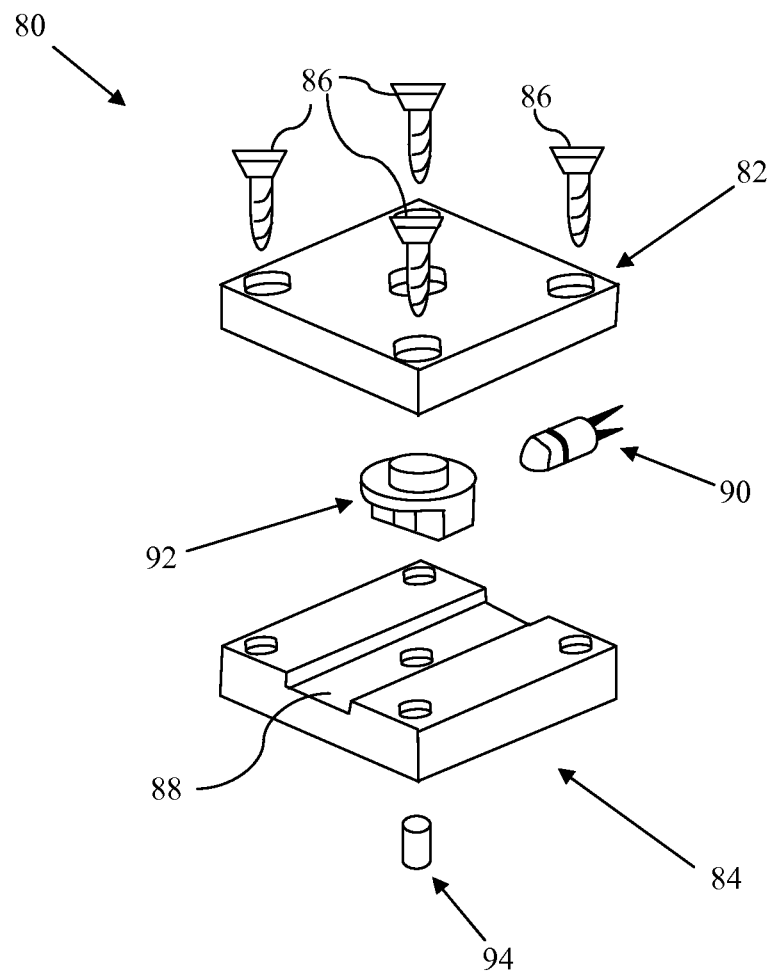
FIG. 4 is a schematic of an illustrative holder for a vibrating motor assembly that vibrates a sample substrate for disaggregation according to various aspects of the present invention.

Referring to FIG. 4, a disaggregation holder assembly 80 is illustrated according to various aspects of the present invention. The assembly 80 includes a top plate 82 that secures to a bottom plate 84, e.g., using fasteners 86. In the exemplary illustrated implementation, the bottom plate 84 includes a channel 88 for receiving a motor, e.g., an eccentric mass vibrator motor 90 and a corresponding vibrator cap 92. The mass vibrator motor 90 and a corresponding vibrator cap 92 are positioned in the channel 88 and the top and bottom plates 82, 84 are joined and secured together, e.g., using the fasteners 86. In an illustrative implementation, a spring plunger 94 feeds through the bottom plate 84 into the motor. The spring plunger 94 retains the motor and allows for variable vibration and amplitude control of the motor. Other holder assemblies may alternatively be implemented. The disaggregation holder assembly 80 is positioned so as to be able to transfer vibrational energy to the sample substrate, e.g., at least in the area of sample collection. For instance, the disaggregation holder assembly 80 may be positioned underneath the sample substrate 22 as shown below in FIG. 8.

Figure 5:
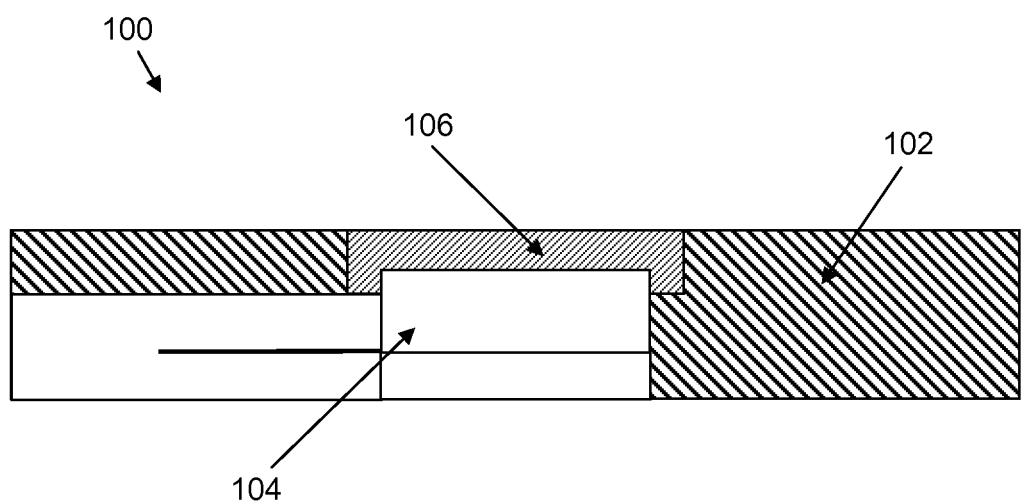
FIG. 5 is a schematic of another illustrative holder for a vibrating motor assembly that vibrates a sample substrate for disaggregation according to various aspects of the present invention.

Referring to FIG. 5, a simplified holder 100 is illustrated according to further aspects of the present invention. The illustrated holder 100 comprises a mounting block 102 that holds a vibrator motor 104 illustrated as a button vibrator motor. The mounting block 102 further positions a vibrator cap 106 above the motor 104. Again, the holder 100 is positioned so as to be able to transfer vibrational energy to the sample substrate, e.g., at least in the area of sample collection. For instance, the holder 100 may be positioned underneath the sample substrate 22 as shown below in FIG. 8.

Figure 6:
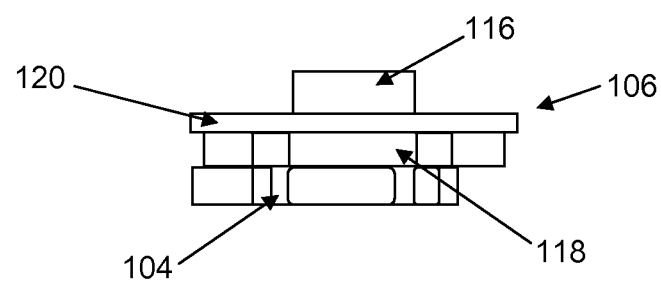
FIG. 6 is a schematic of still another illustrative holder for a vibrating motor assembly that vibrates a sample substrate for disaggregation according to various aspects of the present invention.

Referring to FIG. 6, the vibrator motor 104 and vibrator cap of FIG. 5 is illustrated according to further aspects of the present invention. The vibrator cap 106 comprises an extrusion 116 that localizes vibrations to the collection area of the sample substrate and further minimizes vibration induced into other components of the collector 10. The illustrated vibrator cap 106 further comprises a machined edge 118 that sits in a slot in the holder 100 (FIG. 5) to prevent the vibrator motor 104 from walking around a slot in the holder 100. Similarly, the vibrator cap 106 includes an upper edge 120 that retains the motor 104 in the holder 100. Analogously, the holder 100 is positioned so as to be able to transfer vibrational energy to the sample substrate, e.g., at least in the area of sample collection. For instance, the holder 100 may be positioned underneath the sample substrate 22 as shown below in FIG. 8.

Figure 7:
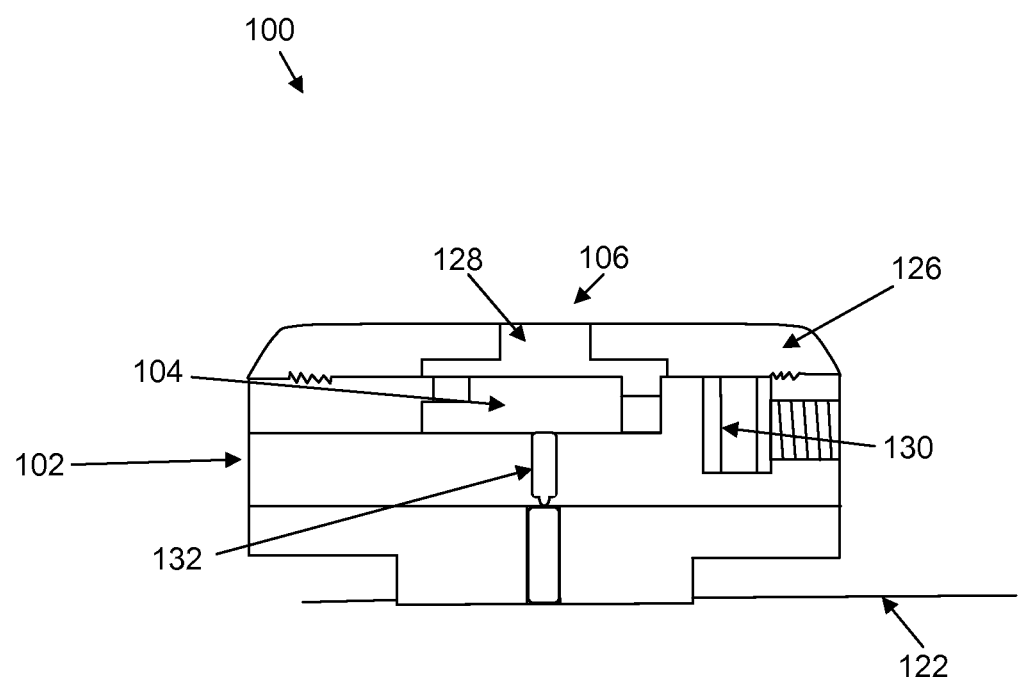
FIG. 7 is a schematic view of a vibrating motor that vibrates a sample substrate for disaggregation according to various aspects of the present invention.

Referring to FIG. 7, an assembly 122 for the vibrator motor 104 and holder 100 for use with a sampling stage of the collector (10, FIG. 1) is illustrated according to further aspects of the invention. The illustrated assembly 122 comprises the mounting block 102 that holds the vibrator motor 104. The mounting block 102 comprises substrate mounting surface 126 that couples to the sample substrate 22. The mounting block 102 also supports the vibrator cap 106 that retains vibrations of the motor and localizes vibrations as described more fully herein. The mounting block 102 also supports a vacuum chuck groove 130 and a spring plunger 132 that retains the motor 104 and allows for variable vibration and amplitude control of the motor 104. Still analogously, the holder 100 is positioned so as to be able to transfer vibrational energy to the sample substrate, e.g., at least in the area of sample collection. For instance, the holder 100 may be positioned underneath the sample substrate 22 as shown below in FIG. 8.

Figure 8:
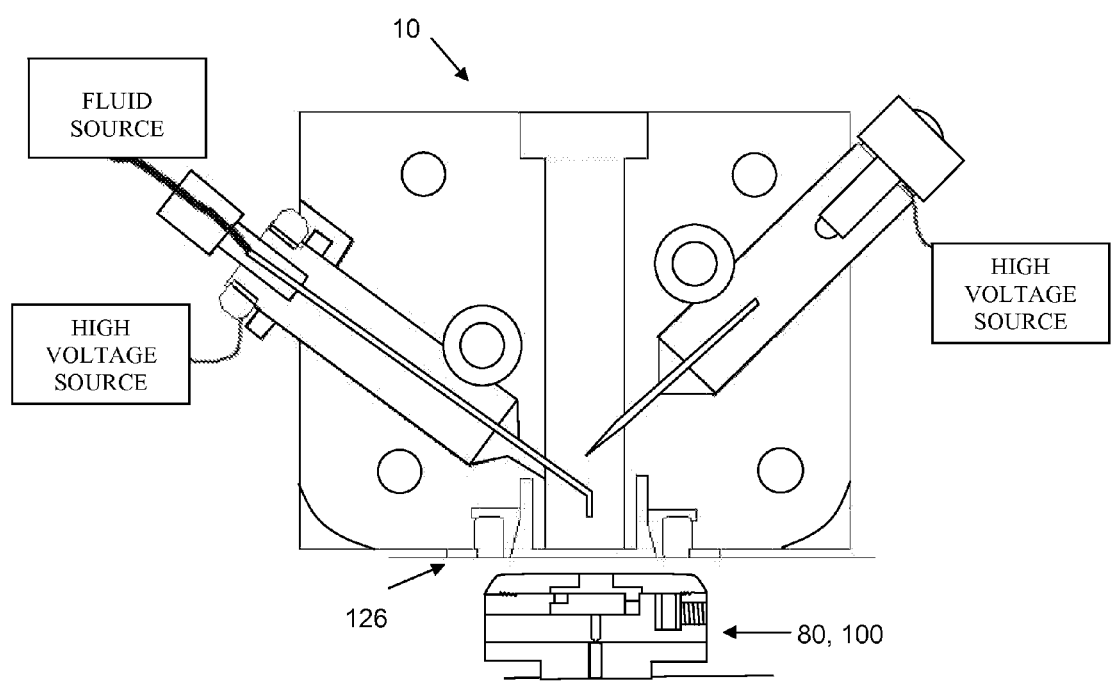
FIG. 8 is a schematic illustration of a motor positioned to vibrate a sample substrate within a device that combines electrostatic collection of aerosol particles and electrohydrodynamic spraying of fluid, according to various aspects of the present invention.

Referring to FIG. 8, a collector system (10, FIG. 1) is illustrated according to various aspects of the present invention. The system is identical to that described with reference to FIG. 1 with the addition of a motor and corresponding holder 80, 100 positioned under the sample substrate 22. As illustrated, the motor holder enables vibration of the sample substrate 22.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. Elements of the embodiments may be combined with elements of other embodiments to create further embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Having thus described the invention of the present application in detail and by reference to embodiments thereof, it will be apparent that modifications and variations are possible without departing from the scope of the invention defined in the appended claims.

What is claimed is:

1. An electrostatic aerosol collector comprising:
   a collector housing;
   an aerosol entry port that provides an inlet for air to flow from outside of the collector housing to the inside of the housing;
   a sample substrate receiving area within the collector housing for receiving a sample substrate including a collection area upon which particulates are collected; a passageway between the aerosol entry port and the sample substrate receiving area;
   a charging device having an electrode;
   a high voltage power source coupled to the charging device; and a spraying device having a spray nozzle that is in a closed space, positioned within at least two concentric cylinders, including an inner concentric cylinder that is a non-conductive cylinder arranged to insulate the charged spray nozzle and the outer concentric cylinder comprises a conductive cylinder;

wherein:
a tip of the electrode creates an electric field defining a charging point in the passageway through which the air passes;
the sample substrate is held at an electric potential that is different from the electric potential of the charging point during particulate collection; and
the spraying device sprays a fluid from the spray nozzle over the collection area of the sample substrate, where the fluid is specifically selected to prepare the collected sample for subsequent evaluation.

2. The electrostatic aerosol collector according to claim 1, wherein the outer concentric cylinder defines a grounded sleeve that is spaced from the inner cylinder and surrounds an exit of the spray nozzle.

3. An electrostatic aerosol collector comprising:
a collector housing;
an aerosol entry port that provides an inlet for air to flow from outside of the collector housing to the inside of the housing;
a sample substrate receiving area within the collector housing for receiving a sample substrate including a collection area upon which particulates are collected;
a passageway between the aerosol entry port and the sample substrate receiving area;
a charging device having an electrode;
a high voltage power source coupled to the charging device;
a spraying device having a spray nozzle; and
a holder positioned so as to be able to transfer vibrational energy to the sample substrate, the holder comprising:
a mounting block that holds a vibrator motor; and
a vibrator cap supported by the mounting block over the motor;
wherein:
a tip of the electrode creates an electric field defining a charging point in the passageway through which the air passes;
the sample substrate is held at an electric potential that is different from the electric potential of the charging point during particulate collection; and
the spraying device sprays a fluid from the spray nozzle over the collection area of the sample substrate, where the fluid is specifically selected to prepare the collected sample for subsequent evaluation.

4. The small area electrostatic aerosol collector according to claim 3, wherein:
the vibrator cap further comprises an extrusion that localizes vibrations to the collection area of the sample substrate and further minimizes vibration induced into the collector.

5. The small area electrostatic aerosol collector according to claim 3, wherein the vibrator cap further comprises:
an edge that sits the housing to prevent vibrations from walking around the holder; and
an upper edge that retains the motor in the holder.

6. The small area electrostatic aerosol collector according to claim 3, wherein:
the mounting block includes a substrate mounting surface that couples to the sample substrate and a vacuum chuck groove; and the vibrator cap retains vibrations of the vibrator motor and localizes vibrations to the area of the sample substrate; and further comprising:
a spring plunger that retains the vibrator motor with respect to the mounting block and allows for variable vibration and amplitude control of the vibrator motor.

7. An electrostatic aerosol collector comprising:
a collector housing;
an aerosol entry port that provides an inlet for air to flow from outside of the collector housing to the inside of the housing;
a sample substrate receiving area within the collector housing for receiving a sample substrate including a collection area upon which particulates are collected;
a passageway between the aerosol entry port and the sample substrate receiving area;
a charging device having an electrode;
a high voltage power source coupled to the charging device; and
a spraying device having a spray nozzle that is enclosed in close proximity to a nonconductive cylinder where the nonconductive cylinder is positioned within a conductive cylinder;
wherein:
a tip of the electrode creates an electric field defining a charging point in the passageway through which the air passes;
the sample substrate is held at an electric potential that is different from the electric potential of the charging point during particulate collection; and
the spraying device sprays a fluid from the spray nozzle over the collection area of the sample substrate, where the fluid is specifically selected to prepare the collected sample for subsequent evaluation.

8. The electrostatic aerosol collector according to claim 7 further comprising:
a controller for controlling the charging device and the spraying device such that the charging device and spraying device operate in alternating fashion.

9. The electrostatic aerosol collector according to claim 8, wherein:
the controller holds the charging device at a high voltage when the spraying device is being operated at an operating potential of the spraying device, and
the controller holds the spraying device at a high voltage when the charging device is being operated at an operating potential of the charging device,
wherein:
the high voltage of the spraying device is selected to avoid conduction between the charging device and the spraying device, and
the high voltage of the charging device is selected to avoid conduction between the charging device and the spraying device.

10. The electrostatic aerosol collector according to claim 9, wherein:
the high voltage set by the controller to hold the charging device is less than the operating potential of the charging device; and
the high voltage set by the controller to hold the spraying device is less than the operating potential of the spraying device.

11. The electrostatic aerosol collector according to claim 7 further comprising:

a controller for controlling the charging device and the spraying device such that the charging device and spraying device operate substantially simultaneously.

12. The electrostatic aerosol collector according to claim 7, wherein:
a high voltage source is coupled to the spraying device; and
at least 6 millimeters separates the spray nozzle from the electrode.

13. The electrostatic aerosol collector according to claim 7, wherein:
the spray nozzle of the spraying device includes a bend therein;
the bend of the spray nozzle is along the length of the spray nozzle,
the spray nozzle is positioned within the passageway such that the spray nozzle enters the passageway at an angle, and
an exit of the spray nozzle points substantially down towards the collection area of the sample substrate.

14. The electrostatic aerosol collector according to claim 7, wherein:
an exit of the spray nozzle is closer to the collection area of the sample substrate than a tip of the electrode.

15. The electrostatic aerosol collector according to claim 7, wherein:
the electrode and the spray nozzle enter the passageway from substantially opposite sides of the passageway such that only a tip of the electrode and an exit of the spray nozzle extend at least substantially to the center of the passageway, above of the sample collection area.

16. The electrostatic aerosol collector according to 7, wherein:
the fluid sprayed by the spraying device at least one of: disaggregates clusters of the collected biological material and desalinizes the collected biological materials collected within the collection area of the sample substrate.

17. The small area electrostatic aerosol collector according to claim 7, wherein:
the fluid injected by the spraying device comprises at least water and ethanol.

18. The electrostatic aerosol collector according to claim 7, wherein a spray pattern of the spraying device is controlled by at least one of:
the flow rate of the corresponding fluid;
the angle of the needle implementing the spray nozzle; and
the geometry of the exit of the spray nozzle.

19. The electrostatic aerosol collector according to claim 7 further comprising:
a motor positioned under the sample substrate that is operable to vibrate so as to cause disaggregation of clusters of the collected biological material collected within the collection area of the sample substrate.

* * * * *